United States Patent [19]

Simon et al.

[11] Patent Number: 4,594,509
[45] Date of Patent: Jun. 10, 1986

[54] INFRARED SPECTROMETER

[75] Inventors: Arno Simon, Ettlingen; Jürgen Gast, Rheinstetten, both of Fed. Rep. of Germany

[73] Assignee: Bruker Analytische Messtechnik GmbH, Fed. Rep. of Germany

[21] Appl. No.: 574,862

[22] Filed: Jan. 30, 1984

[30] Foreign Application Priority Data

Jan. 31, 1983 [DE] Fed. Rep. of Germany ....... 3303140

[51] Int. Cl.⁴ ............................................. G01J 1/00
[52] U.S. Cl. ..................................... 250/338; 250/353
[58] Field of Search ..................... 250/338, 339, 353; 350/527, 505

[56] References Cited

U.S. PATENT DOCUMENTS

| | | | |
|---|---|---|---|
| 3,206,603 | 9/1965 | Mauro | 250/338 |
| 3,803,413 | 4/1974 | Vanzetti et al. | 250/338 |
| 3,827,811 | 8/1974 | Kato et al. | 350/527 |
| 3,868,185 | 2/1975 | Genzel et al. | 250/339 |
| 4,130,757 | 12/1978 | Frasher et al. | 350/505 |
| 4,241,390 | 12/1980 | Markle et al. | 350/505 |
| 4,395,095 | 7/1983 | Aorton | 350/505 |
| 4,429,225 | 1/1984 | Fumoto et al. | 250/339 |
| 4,479,058 | 10/1984 | Gast et al. | 250/353 |

OTHER PUBLICATIONS

"The NanoSpec/20IR", two publications of Nanometrics, Inc.

Primary Examiner—Alfred E. Smith
Assistant Examiner—Richard Hanig
Attorney, Agent, or Firm—Harness, Dickey & Pierce

[57] ABSTRACT

An infrared spectrometer comprises first optical means for focussing a beam of light in a point-shaped area of a sample (19), second optical means for focussing upon a detector (26) the light emitted by the sample, and third optical means permitting the visual observation of the point-shaped area (19). The second optical means of this arrangement are so designed that they pick up the light reflected by the point-shaped area (19). The arrangement of the invention permits measurements to be performed on extremely small areas and even on samples which are not or hardly pervious to light in the infrared range.

31 Claims, 12 Drawing Figures

INFRARED SPECTROMETER

The present invention sets out from an infrared spectrometer comprising first optical means for focussing a beam of light in an at least approximately point-shaped area of a sample, second optical means for focussing upon a detector the light emitted by the sample, and third optical means permitting the visual observation of the at least approximately point-shaped area.

It has been known in the art to use infrared spectroscopy for investigating in particular liquid and gaseous samples the infrared measurements permitting conclusions as to the molecular structure of the sample under investigation. The samples investigated in usual infrared spectrometers are of a macroscopic size, for instance in the range of a few cubic centimeters. The measurement is performed on the whole sample and does not differentiate between possible differences between different areas of the sample.

Further, the publication "The Nanospec/20 IR" published by the Nanometrics company describes an infrared measuring arrangement permitting so-called "micro-measurements". This arrangement uses a Nernst needle for illuminating a plane which can be adjusted along two coordinates and which is intended for receiving a sample, via a beam path which comprises several mirror lenses and deflecting mirrors and which can be interrupted by an aperture plate and influenced by a stepped filter disk. The light emitted by the Nernst needle is focussed upon one point of the sample, the light passing through the sample is concentrated and focussed upon a detector. A deviating mirror which is located between the elements for concentrating the transmitted light and the detector comprises a rectangular aperture through which the light arriving from the sample passes on its way to the detector. The mirror provided with the rectangular aperture can be visually observed via an eyepiece. The point of the sample upon which the light is focussed is located in the area of the rectangular aperture and cannot, therefore, be visually observed.

Although it is possible in this manner to carry out investigations on microscopically point-shaped areas of a sample it is a drawback of the arrangement that it is suited only for transmission measurements so that investigations can be performed by the arrangement only on samples which a sufficiently pervious to infrared light.

Another disadvantage of the known arrangement is to be seen in the fact that exactly that point of the sample which is to be investigated cannot be visually observed so that one select the point under unvestigation "blind" by displacing the plane of the sample.

It is still another disadvantage of the known arrangement that the filter disk located within the path of the beam permits only a very limited resolution because it represents a so-called "wedge filter" in which the pass range varies continuously over the filter circumference. Accordingly, the resolution achievable is a function of the gap width used and deteriorates as the gap width increases. On the other hand, however, the signal amplitude rises as the gap width increases so that a poor resolution can be achieved only with certain substances which due to the signal amplitude obtainable require a great gap width. Typically, the resolution achievable with such wedge filters is in the range of some per mils to 1 percent of the band width of the filter used.

However, this band width achievable in the known arrangement is absolutely insufficient for measuring gases or inorganic substances.

Another disadvantage of the known arrangement lies in the fact that the dispersive measuring method employed makes it necessary to scan the spectral lines slowly one after the other so that the signal output obtainable per time unit is relatively low.

Finally, it is a substantial disadvantage of the known arrangement that the spectrum covered must be calibrated before each measurement to permit the spectral lines measured to be related to a wave-number scale.

Now, it is the object of the present invention to provide an improved infrared spectrometer of the type described above which permits a substantially greater number of sample substances to be investigated.

According to the present invention, this object is achieved in that the second optical means pick up the light reflected by the at least approximately point-shaped area.

For the purposes of the present context, the term "light" is used to describe any type of usable electromagnetic radiation, including that in the non-visible range, and the term "at least approximately point-shaped area" is meant to describe an area of abt. 20 $\mu$m to 1 mm in diameter.

Thus, the spectrometer of the invention offers the considerable advantage that measurements can be carried out even on solid bodies or liquids which are not or only poorly pervious to infrared light. This opens up a large variety of applications, for instance in semiconductor technology, because the spectrometer of the invention is the first to offer the possibility to measure out by points any existing defects in the surfaces of substrates or semiconductors in the microscopical range. Another important field of application of the spectrometer of the invention is to be found in forensic analytics, i.e. the forensic investigation of samples, such as finger prints or the like. If the latter are found directly on a carrier which is impervious to light they can be measured out only by the reflection method.

In one embodiment of the invention, an intermediate focus is formed on the sample with an adjustable focal aperture being preferably arranged in the area of such intermediate focus. This permits the infrared light to be radiated with great precision upon individual points of the sample so that highly selective measurements are rendered possible.

Depending on the desired selectivity, different focal apertures can be conveniently chosen, for instance by exchanging firmly adjusted aperture diaphragms or by using conventional continuously variable aperture diaphragms. The latter may have a circular cross-section as known from photographic apparatuses. On the other hand, crossed slit diaphragms may also be used in which case a rectangular aperture is obtained. The size and/or shape of the aperture is selected with regard to the nature of the point-shaped sample area to be investigated.

In a preferred improvement of the invention, intermediate focussing is realised in a particularly simple way in that the light beam arriving from the infrared light source in the usual parallel orientation is focussed by a collimator mirror.

For focussing the diverging beam of light emerging from the diaphragm, one improvement of the invention uses a mirror lens which gives a particularly satisfactory image of the intermediate focus in that a point-shaped area of particularly small dimensions is illuminated only.

It is of course also possible to use a lens system instead of the mirror lens provided the optical properties of the lens system are suited for infrared light.

In certain alternative improvements of the invention, the converging beam of light impinging upon the sample may by oriented at a right or oblique angle relative to the surface of the sample. When oriented at a right angle, it is the directly reflected light which is predominantly picked up, while in the case of the oblique orientation the diffuse reflected light is picked up if no additional optical means are provided.

In both cases, the arrangement of the optical means is selected according to a preferred improvement of the invention in such a manner that several of the optical means serve on the one hand to radiate the light upon the sample and, on the other hand, to receive the light reflected by the sample. This arrangement permits an especially compact and, regarding the number of components used, economic design.

The required separation of the reflected light from the radiated light is achieved in one embodiment of the invention in that immediately before reaching the aperture the reflected light is focussed upon a detector by a deviating mirror and a collimator mirror. However, it is also possible according to the invention to use an pivotally mounted beam splitter instead of the deviating mirror which offers the advantage of lower light losses as compared with a pivotally mounted deviating mirror.

According to a further improvement of the invention the mirror lens system of the first optical means may, however, also comprise a first mirror lens for parallelizing the diverging beam of light emerging from the diaphragm aperture and a second mirror lens for focussing the parallelized beam of light, the second optical means being provided with a deviating mirror which is arranged in the parallelized beam of light and which can be oriented about an axis located preferably outside the parallelized beam of light, for deviating the light deflected by the second mirror lens towards the diaphragm aperture.

This offers the advantage that no deflection of a light beam occurs near the diaphragm aperture, i.e. in an area where the beam of light is already largely focussed so that small mirrors and great mechanical precision are required, but that rather an intermediate step is used to produce a parallelized beam of light which can be made wide enough to render the deviation easy.

Alternatively, however, it is also possible to use an annular mirror arranged at an oblique angle relative to the optical axis, in the area between the sample and the diaphragm aperture. Such an annular mirror will substantially pick up the diffuse reflected light, and the beam of light deviated by the annular mirror will be directed to a detector, preferable via a deviating mirror.

According to another improvement of the invention, the diffuse reflected light is directly picked up by a mirror arranged in the dark space of the mirror lens system which focusses the infrared light upon the sample. Preferably, the beam of light deviated by the deviating mirror is focussed upon a detector through a collimator mirror.

If an additional mirror lens or lens system is provided above the surface of the sample, in addition to the mirror lens or lens system focussing the light upon the sample, then the diffuse reflected light obtained when the light is vertically radiated upon the sample can be picked up by the second mirror lens or lens system. When the light is radiated upon the sample at an oblique angle, the directly reflected light can be picked up also in this manner. The arrangement using two mirror lenses or lens systems provides increased variability, for instance in that the direct and diffuse reflected light can be measured out simultaneously. In addition, different images can be formed in the beam paths of the incoming and reflected light if a second optical system of this type is used. In the last-mentioned case it is advantageous to provide a separate unit arranged vertically to the sample surface, for observing and illuminating the point-shaped sample area.

The beam of light reflected by the sample and received by the mirror lens or lens system is preferably directed to a deviating mirror and from the latter to a detector.

For visually observing the point-shaped area under investigation, a preferred improvement of the invention provides that an image is formed of the point-shaped area in the third optical means serving this purpose. As compared with the prior art, this offers the considerable advantage that the point to be investigated can be directly visually observed, in some improved embodiments of the invention even during the measurement, which permits the point under investigation to be "selected" with much greater precision. This is particularly important for investigations of microscopically point-shaped areas because even smallest misadjustments may in this case result in considerable measuring errors, for instance in the example mentioned at the outset where defects in semiconductor surfaces are to be investigated.

The third optical means provided for the visual observation comprise conveniently an ocular or a binocular of a conventional type.

To permit visual observation by several persons, a preferred improvement of the invention uses a projection screen, in particular a ground glass screen. This also permits the sample area under investigation to be photographed for documentary purposes.

In a further improvement of the invention, an electronic device may be provided, either alternatively or additionally, for visually observing the sample, for instance by means of a charge-coupled device (CCD) which permits an image to be optically picked up line by line so that the microscopically point-shaped sample area being observed and investigated can be viewed on a usual television monitor and recorded for documentary purposes using conventional video storage means.

For coupling out from the beam path the light required for the third optical means, for visually observing the sample, impervious or semi-pervious mirrors may be used. Depending on the mirror position, the impervious mirrors should conveniently be pivotally mounted so that they can be moved out of the beam path. In certain measurements, this is recommended also for semi-pervious mirrors, as in spite of being pervious they entail quite considerable losses in radiation energy, a phenomenon which is undesirable for certain measurements.

The deviating mirror used for coupling out a beam for the third optical means may be arranged directly in the area of entry, i.e. behind the first collimator mirror, but it is also possible to arrange it behind the diaphragm aperture or, if an additional mirror lens is used above the sample surface, behind the said additional mirror lens and the associated detector.

For visually observing the point-shaped area under investigation, one may firstly use the light emitted by the infrared light source provided the latter comprises some components in the visible range. This requirement need not be fulfilled if an electronic photoelectric transducer is used on the condition that the transducer is capable of operating in the infrared range.

However, according to a further improvement of the invention it is also possible to illuminate the surface of the sample by an external light source emitting light in the visible range. It goes without saying that in this case the spectral distribution of the light source must be selected to ensure that any infrared measurements carried out in parallel are not disturbed. It is, however, also imaginable to switch the light source off during the measurements so as to avoid any possible disturbances.

Particularly flexible measurements are rendered possible by a preferred improvement of the invention in which the optical elements, in particular the mirror lenses, lens systems and/or collimator mirrors are provided in several different designs so that at any time the most suitable element can be introduced into the beam path by means of a turret or slide arrangement. This permits a large plurality of image scales to be adjusted so that larger or smaller point-shaped areas can be investigated at desire. In cases where the sample consists of a material which is pervious or partly pervious to infrared light a transmission measurement may be performed in parallel with the before-described reflection measurement on the condition that, according to a preferred improvement of the invention, additional optical means for receiving the transmitted light are arranged below the sample. Such an arrangement permits comparative reflection and transmission measurements to be carried out at the same time and on the same point of the sample.

The semi-pervious mirrors located in the beam path are preferably displaced out of the beam path during such transmission measurements so as not to dim unduly the incoming light beam.

The dimensions of the "point-shaped" area are substantially determined in point measurements by the resolution of the lenses, and are for instance equal to 20 $\mu$m. According to the invention, it is however also possible to investigate a small approximately point-shaped area, typically of a diameter of less than 1 mm, instead of illuminating merely a point if possible.

Such a small approximately point-shaped area of finite dimensions is preferably projected upon a plurality of detector elements, either a series of individual detector elements or a surface detector comprising a matrix of detector elements, the outputs of which can be processed by an evaluator in an integrating or selective manner. In this variant of the invention, the measuring values recorded by the matrix can be displayed on a monitor either in their totality or by sectors, and even the simultaneous evaluation of several measuring points is possible in accordance with the invention.

The measures described before offer the substantial advantage that a measuring point need not be exactly adjusted, but that instead one can select certain of the the measuring points of the matrix without the need to displace the sample or the measuring device mechanically within the matrix for the purpose of performing such selection.

The method of the invention to effect reflection measurements on point-shaped sample areas leads naturally to a low signal amplitude because only a small portion of the light is reflected upon the detector, depending on the reflection coefficient and the surface properties of the material of the sample under investigation. A particularly preferred improvement of the invention provides, therefore, for such measurements with low signal levels a measuring method making use of the Fourier transformation. It is the special aspect of this method that contrary to the dispersive measurement of the known arrangement described above, all spectral lines are activated simultaneously and the spectrum to be measured is obtained by conversion from the time domain to the frequency domain. Thus, a considerably higher signal output is obtained per time unit of the measurement so that a considerably higher signal-to-noise ratio can be achieved in the same measuring period. On the other hand, the simultaneous excitation of all measuring frequencies renders the cross-sectional shape of the employed beam of light uncritical because—unlike the conditions of the known spectrometer—no different pass ranges of a wedge filter are involved. Accordingly, very high resolutions can be obtained with the FT method, which permits even gases and inorganic materials to be measured with high precision. The FT method permits measurements with particularly high signal-to-noise ratios even in cases of extremely low signal levels. In this manner, the natural disadvantages encountered in reflection measurements of point-shaped areas, i.e. the lower signal output, can be efficiently compensated so that the invention provides altogether an exceptionally effective and, as regards its applications, versatile measuring method.

Other advantages of the invention will become apparent from the specification and the attached drawing.

The invention will be described hereafter in detail with reference to the drawing in which.

Figures 1, 2:
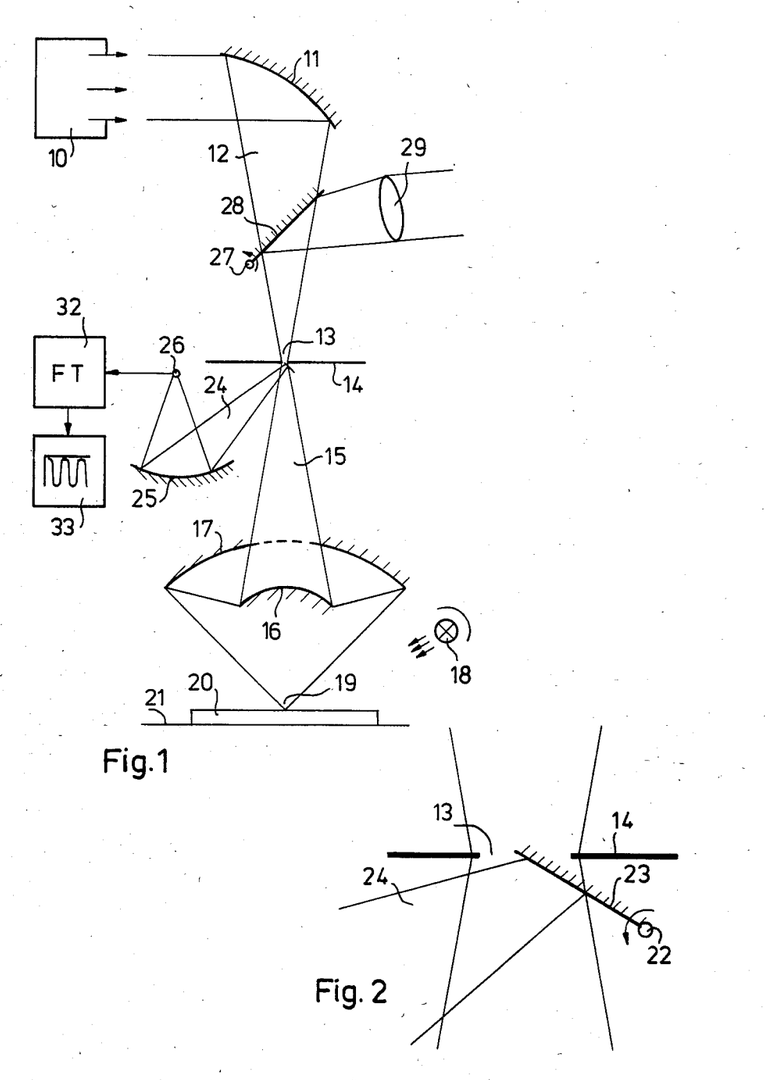
FIG. 1 shows a beam path of a first embodiment of a spectrometer of the invention.
FIG. 2 is an enlarged detail of the diaphragm area of the beam path of FIG. 1.

In the beam path of a first embodiment of a spectrometer in accordance with the invention shown in FIG. 1, 10 is used to identify an infrared light source emitting a substantially parallel light beam. The parallel light beam is directed towards a collimator mirror 11 and deviated by the latter to form a converging beam of light 12. The beam of light 12 is focussed upon a diaphragm aperture 13 in a plate 14. In the simplest of all cases, the diaphragm aperture 13 is formed by an aperture in the plate 14, but it is also possible according to the invention to provide a variable aperture 13. This may be achieved for instance by providing a set of permanently adjusted exchangeable diaphragms, or else continuously variable diaphragms may be used, for instance such having a circular cross-section and radially movable segments or such having a rectangular cross-section formed by disposing two slit diaphragms one behind the other and in vertical relationship relative to each other.

After having passed the diaphragm aperture 13, the now diverging beam of light 15 impinges upon a mirror lens 16, 17 which focusses the incoming diverging beam of light 15 upon a point-shaped area 19 of a sample 20 arranged on a carrier 21.

In one further improvement of the invention, the sample 20 is additionally illuminated by a light source 18 emitting light in the visible range, it being preferably possible to switch off the light source 18 during the measurement.

Due to the fact that the axis of the beam of light focussed upon the sample 20 extends at a right angle relative to the sample surface, the light directly reflected by the sample 20 is returned along the path just described and encounters on this way a deviating mirror 23 which is arranged immediately before the diaphragm aperture 13 and can preferably be pivoted about an axis 22—as can be seen in detail in FIG. 2. The deviating mirror 23 covers for instance 50% of the diaphragm opening 13 and reflects the light arriving from the mirror lens 16, 17 to form a diverging beam of light 24 which is focussed by a collimator mirror 25 upon a detector 26. It goes without saying that the pivotally mounted deviating mirror may be replaced in this example, just as in all the other examples, by a slidingly mounted deviating mirror.

The detector 26 now transforms the incoming measuring light into a corresponding electric signal and supplies the latter to a computer which, preferably, processes it using the Fourier transformation (FT). The computer 32 comprises further a display 33 which permits the measured infrared spectrum to be viewed, printed out or recorded in any other manner for documentary purposes. The display may for example take the form of a screen or recorder.

Finally, an additional deviating mirror 28 which is preferably mounted to swing about an axis 27 is provided in the area between the diaphragm aperture 13 and the collimator mirror 11, for deviating the beam of light arriving from the mirror lens 16, 17 towards a visual observation unit as indicated by the lens 29.

As is easily apparent from the beam path shown in FIG. 1, an image is formed of the aperture diaphragm 13 on the sample 20 at the image scale of the mirror lens 16, 17. In a typical embodiment of the invention, the image scale of the mirror lens 16, 17 is 15 so that when the diaphragm aperture is 1 mm in diameter the point-shaped area 19 obtained has a diameter of 70 $\mu$m. Accordingly, the projection of the diaphragm aperture 13 leads to extremely small point-shaped areas 19 and, as a result thereof, to a high geometric resolution as regards the point-shaped measurement performed on the sample 20.

Thus, the diaphragm aperture 13 defines by the said image on the one hand the point-shaped area 19 on the sample 20, and on the other hand simultaneously the area visually observed through the lens, so that the measuring area and the observed area are generally identical in the arrangement of the invention.

Figure 3:
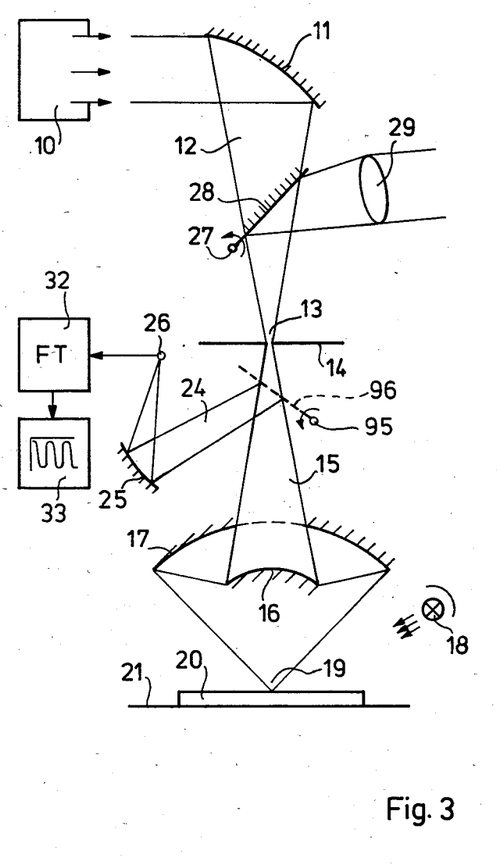
FIG. 3 shows a variant of the embodiment shown in FIG. 1, using a beam splitter instead of a folding mirror.

The embodiment of FIG. 3 differs from that shown in FIGS. 1 and 2 in that a beam splitter 96 which can be pivoted about an axis 95 is provided instead of the deviating mirror 23 mounted to swing about the axis 22. The beam splitter 96 is also arranged near the diaphragm aperture 13, but not as near as the deviating mirror 23 in FIGS. 1 and 2.

The beam splitter 96 reflects for instance 50% of the light arriving from the mirror lens 16, 17 into the diverging beam of light 24 which is then focussed by the collimator mirror 25 upon the detector 26.

Figure 4:
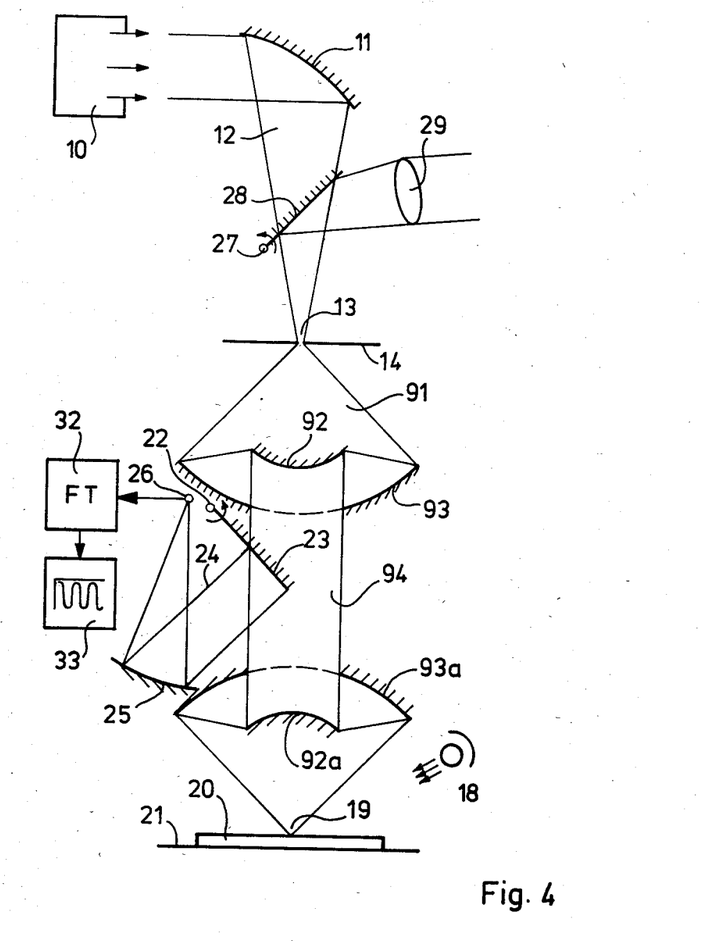
FIG. 4 shows another variant of the embodiment of FIG. 1 in which a parallel beam of light is produced in an intermediate step.

FIG. 4 shows another variant which accounts for the problem of the limited space available in the immediate neighbourhood of the diaphragm aperture 13 by making the diverging beam of light 91 obtained after passage of the diaphragm aperture 13 incide upon a mirror lens 92, 93 which transforms the diverging beam of light 91 into a parallelized beam of light 94. The latter is then directed towards a complementary mirror lens 92a, 93a which focusses the radiation again upon the at least approximately point-shaped area 19 of the sample 20.

The light directly reflected by the sample 20 is then returned in the manner described above and incides on its way upon the deviating mirror 23 which is now located in front of the mirror lens 92, 93 and preferably mounted to swing about an axis 22 located outside the parallelized beam of light 94. The deviating mirror 23 covers in this variant for instance 50% of the parallelized beam of light 94 and reflects the incident light into the diverging beam of light 24 which is again focussed upon the detector 26 by the collimator mirror 25.

Figures 5, 6:
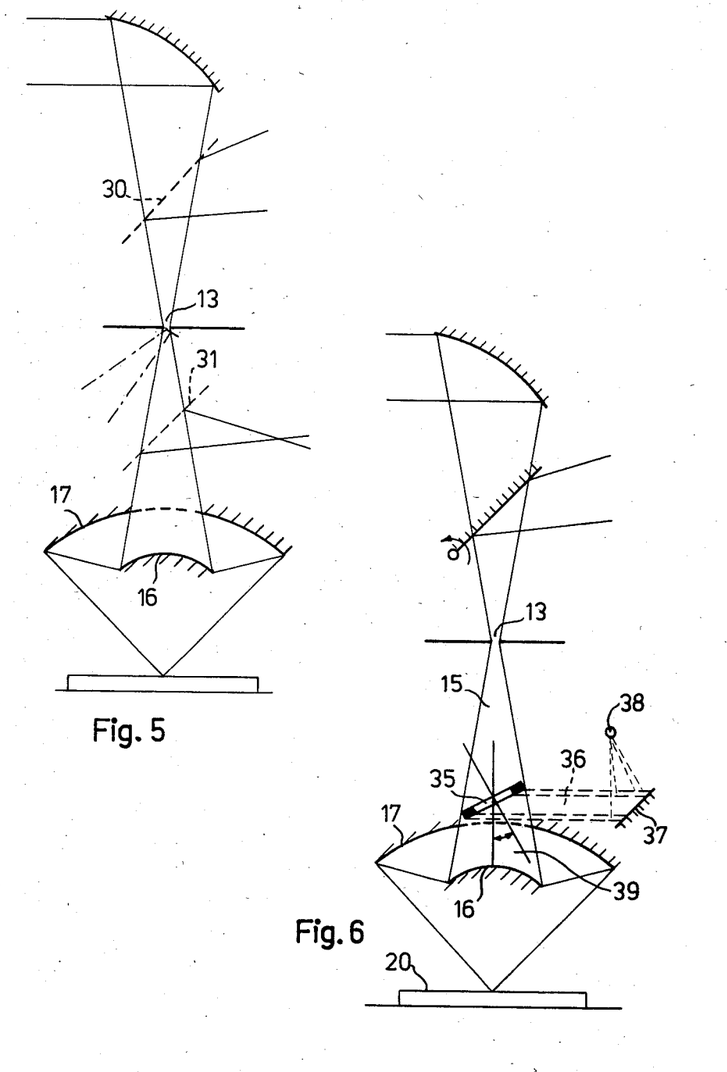
FIG. 5 shows a beam path of a second example of a spectrometer in accordance with the invention.
FIG. 6 shows a beam path of a third example of a spectrometer in accordance with the invention.

In the embodiment shown in FIG. 5 the beam path of the incoming infrared light and of the reflected light are generally unchanged, with the exception that the visual observation means are differently designed in that the impervious deviating mirror 28 of FIG. 2 has been replaced by a semi-pervious mirror 30 which is, however, located at the same position. Alternatively, the semi-pervious mirror may also be provided between the diaphragm aperture 13 and the mirror lens 16, 17, as indicated by 31 in FIG. 5. It need not be stressed in this connection that the optical means for visually observing the sample may of course be designed in any conventional manner with due regard to the position of the mirrors 28, 30, 31.

In contrast, the example of FIG. 6 uses an arrangement in which the diffuse radiation reflected by the sample 20 is received and evaluated. For this purpose, an annular mirror 35, the axis of which extends at an angle 39 to the axis of the beam of light 15, is arranged in the area of the diverging beam of light 15 between the diaphragm aperture 13 and the mirror lens 16, 17. The beam of light 36 deviated by the annular mirror 35 is focussed upon the detector 38 by a deviating mirror 37.

The arrangement shown in FIG. 6 will now be explained in detail with reference to the simplified example shown in FIG. 7. In this example, an incoming parallel beam 40 is partly shaded off by an annular mirror 41 so that shaded areas 42, 43 are obtained. The axis of the annular mirror 41 is again inclined relative to the axis of the beam 40. The beam incides upon a lens 44 and is concentrated by the latter so that the beam is focussed upon an at least approximately point-shaped area 46 of a sample. A beam 45 inciding upon the area 46 outside the centre axis, at an angle, is on the one hand directly reflected and returned via the non-shaded area, but a beam 47 resulting from diffuse reflection is directed, for instance, into the shaded area and from there to the bottom face of the annular mirror 41 which has its surface 48 facing towards the area 46 provided with a reflecting coating. Accordingly, the annular mirror 41 acts to deviated from the direction of the beam 40 only that radiation which has been reflected in a diffuse manner by the area 46 of the sample.

The arrangement of FIG. 6 uses the same principle, i.e. the annular mirror 35 deviates in exactly the same manner, but here by the mirror lens 16, 17, only the radiation obtained by diffuse reflection from the sample 20 in the form of the beam of light 36 so that only the diffuse reflected radiation is received by the detector 38.

Figures 7, 8:
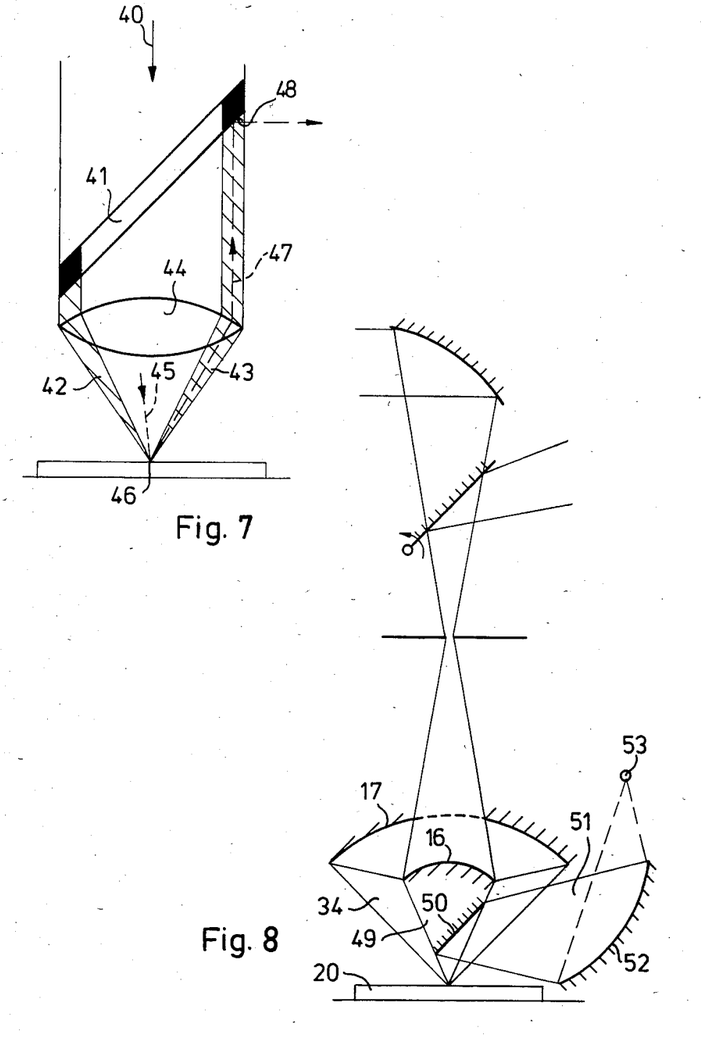
FIG. 7 is a diagrammatic representation illustrating the function of the annular mirror used in the beam path of FIG. 6.
FIG. 8 shows a beam path of a fourth example of a spectrometer in accordance with the invention.

Another arrangement for measuring diffuse reflection is shown in FIG. 8. The embodiment shown there benefits of the fact that the mirror lens 16, 17 focusses upon the sample 20 a beam of light 34 of toroidal cross-section. Accordingly, there remains a so-called dark space 49 in the centre of the said toroidal beam of light 34. This dark space is entered only by diffuse radiation reflected by the sample 20, which is picked up by a deviating mirror 50 and focussed upon a detector 53 by a collimator mirror 52.

As can be seen in FIG. 8, the arrangement shown there is completely independent, for instance from the arrangement shown in FIGS. 1 to 5, so that the measurement of the diffuse reflected radiation can also be effected additionally to, and even in parallel with, the measurement of the direct reflected light, without disturbing the latter measurement in any manner.

Figure 9:
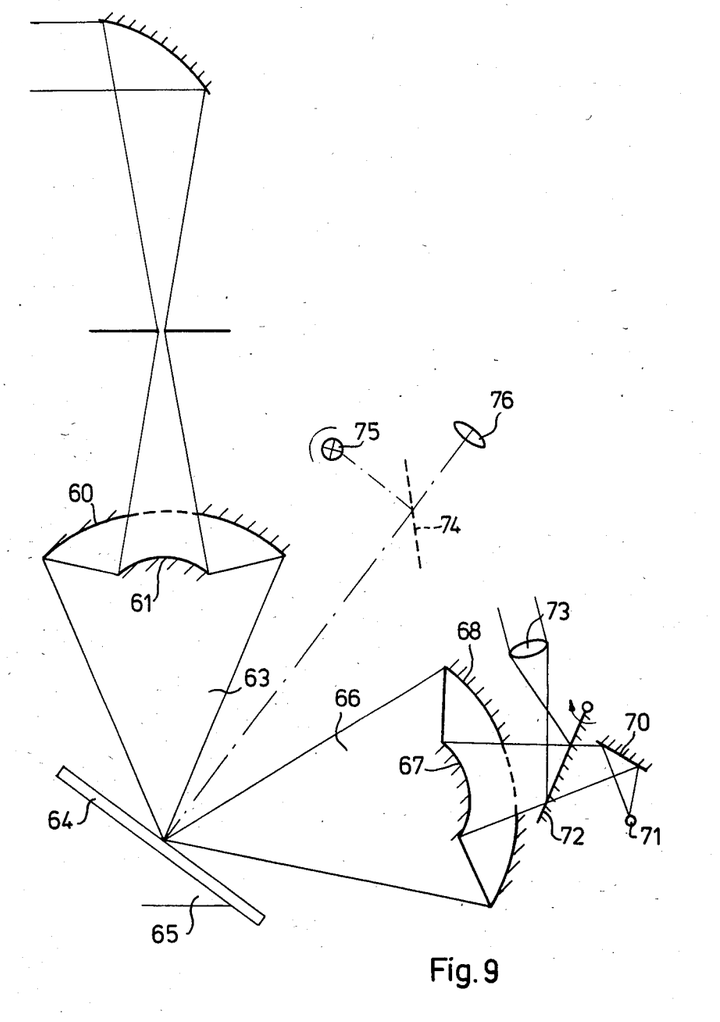
FIG. 9 shows a beam path of a fifth example of a spectrometer in accordance with the invention comprising several optical systems arranged one beside the other above the sample surface.

In the arrangement shown in FIG. 9, a lens 60, 61 produces a beam of light 63 which converges at a more acute angle compared with that of the previous figures and which is focussed upon a sample 64 arranged at an angle 65 relative to the horizontal plane. Accordingly, the angle 65 is identical to the angle by which the axis of the beam of light 63 is displaced from the vertical line to the sample surface. The fact that the beam of light 63 impinges at an angle upon the surface of the sample 64 results in the directly reflected radiation taking a path different from that of the incoming light beam, i.e. being deviated by the surface of the sample 64. The diverging beam of light 66 obtained is then received by another mirror lens 67, 68 and focussed by the latter upon a detector 71, via a deviating mirror 70. In order to permit the visual observation of the point-like area of the sample 64 under investigation a, preferably pivotally mounted, deviating mirror is provided which coacts with a lens 73 which is meant to represent the visual observation unit.

Alternatively, observation means—indicated in the drawing by a lens 76—directed vertically upon the surface of the sample 64 may be provided comprising a semi-pervious mirror 74 which permits on the one hand the point-shaped area to be illuminated via a light source 75 and, on the other hand, the area under investigation to be viewed at a right angle.

Accordingly, the arrangement of FIG. 9 permits to carry out measurements in which the light incides at an acute angle and is reflected at a corresponding angle, the optical means provided for picking up the reflected light being separate from the means used for irradiating the sample.

It is, of course, understood that the arrangement of FIG. 7 can be used also when the orientation of the sample 64 is such that the sample surface extends again vertically to the axis of the converging beam of light 63, as shown in the previous figures. In this case, the separate optical means 67 6o 73 may serve for picking up the diffuse reflected light.

However, the separation of the irradiation on the one hand and the picking up on the other hand of the reflected light permits in both cases the use of, for instance, different image scales so that the visual observation means enable areas to be observed which may even be larger or smaller than those irradiated by the incoming light.

Figure 10:
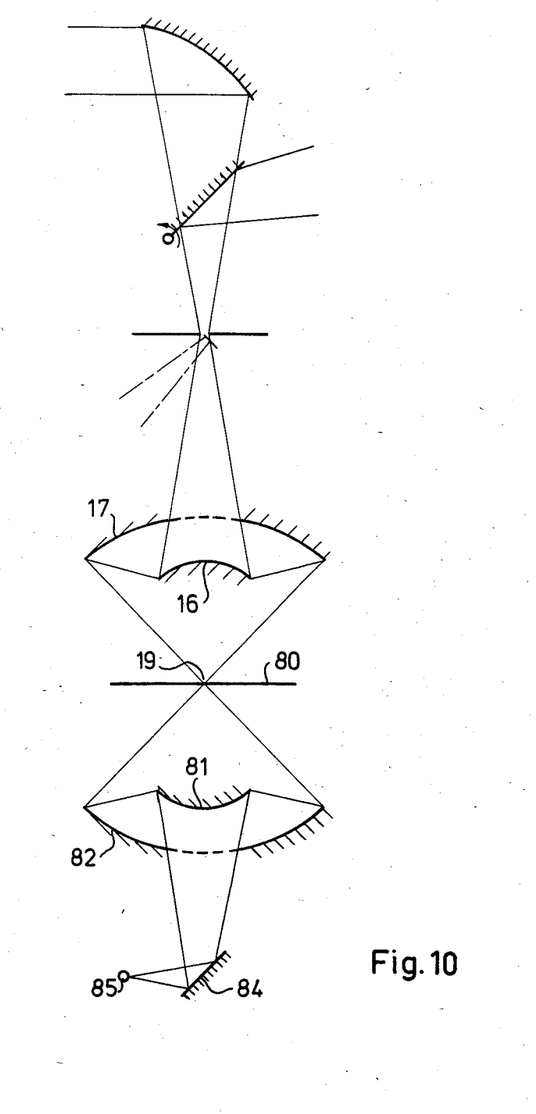
FIG. 10 shows a beam path of a sixth example of a spectrometer in accordance with the invention, permitting reflection and transmission measurements to be simultaneously effected.

In the arrangement of FIG. 10, the arrangement of FIG. 1 is extended insofar as, when a sample 80 is used which is partly or completely pervious to infrared light, simultaneous transmission measurements are rendered possible. For this purpose, an additional optical system consisting for instance of a mirror lens 81, 82, is provided below the sample 80 for focussing the transmitted light upon a detector 85, via a deviating mirror 84.

Accordingly, the arrangement of FIG. 10 permits reflection and transmission measurements to be carried out at the same time and on the same point of the sample.

Figure 11:
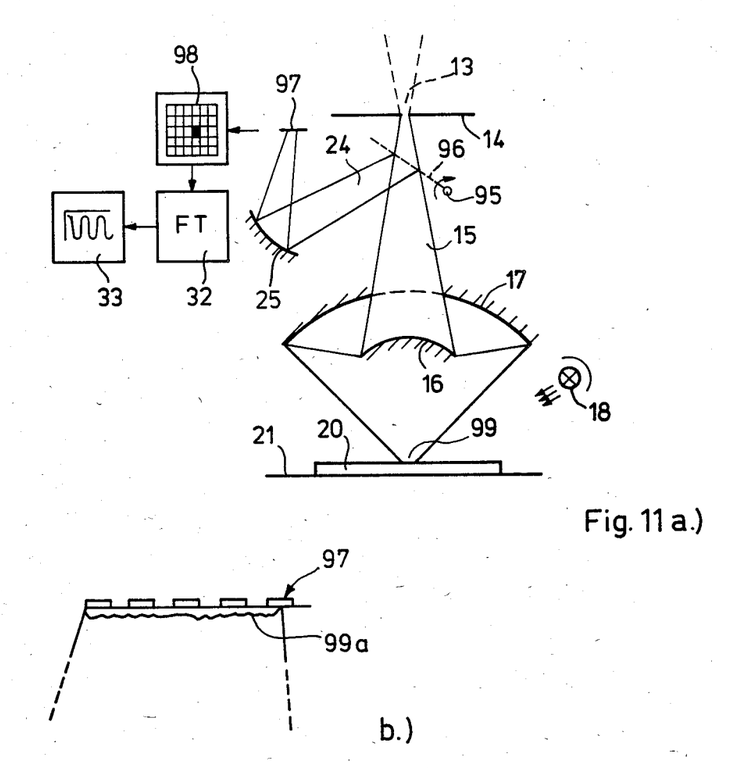
FIG. 11a and 11b shows, a beam path of a seventh example of a spectrometer in accordance with the invention which serves to investigate a surface area of finite dimensions.

Finally, FIGS. 11a and 11b show still another embodiment of the invention in which the area 99 of the sample 22 under investigation has finite dimensions, for instance a diameter of up to approx. 1 mm.

The arrangement corresponds generally to that shown in FIG. 5, which means that a pivotally mounted beam splitter 96 is located in the diverging beam of light 15 coming from the diaphragm aperture 13.

But instead of the detector 26 used in all other examples, a surface detector 97 is used in this case upon which the sample area 99 is projected by the collimator mirror 25, as indicated by 99a in FIG. 11b.

The surface detector 99 may be designed either as a series of detector elements or as two-dimensional matrix, as indicated by 98 in FIG. 11a. When the measuring values of the matrix 98 are displayed on a monitor screen, the user of the spectrometer of the invention has the possibility to select a measuring point, i.e. optimize the definition of the point to be measured within the area 99, without the need to displace the sample 20 mechanically relative to the remaining parts of the spectrometer. Of course, it is also possible to perform integrating or simultaneous discrete measurements through a majority of the detector elements of the matrix 98, or through the whole matrix 98.

In the examples described above, different optical groups have been used for irradiating the light, for picking up the reflected light, for receiving the light for visual observation of the sample, and finally for receiving the transmitted light. All these optical elements, impervious or pervious, deviating or collimator mirrors, mirror lenses or lens systems, have been described before in connection with the different examples in a specific combination. It is, however, understood that different designs of such mirrors, lenses or lens systems and different other combinations thereof are imaginable without departing from the scope of the present invention. So, the impervious mirrors used for deviating the reflected or transmitted light upon the respective detectors could, for instance, be replaced by semi-pervious mirrors.

Further, it is, for instance, well possible to use either extra-axial mirrors or mirror lenses or lens systems, provided such lens systems are suited for the infrared range. If several optical systems are used, it is of course also possible to use a mirror lens in the one and a lens system in the other beam path.

As mentioned already in connection with the examples described, the deviating mirrors used for deviating the reflected light or for deviating the light for visual observation may be arranged on different points of the beam path. Further, it is possible to use impervious or semi-pervious mirrors in accordance with convenience, but if impervious mirrors are used, these should conveniently be mounted to pivot about an axis so that measuring and visual observation can be carried out alternately if the mirrors hinder the other operating mode. Furthermore, the semi-pervious mirrors may also be mounted to pivot about an axis in cases where the radiation losses by abt. 50 percent encountered in these mirrors are undesirable.

For visually observing the selected microscopically point-shaped area of the sample an ocular may be used in the simplest of all cases, which permits one-eyed observation of the point-shaped area of the sample under investigation. Improved observation possibilities are, however, offered by a binocular.

If more than one persons are to be permitted to observe the point-shaped area of the sample or if photographic recording of the area under investigation is desired, the means for visually observing the sample may also take the form of a projection screen or a ground-glass screen which, if photographic recording is required, may be replaced by a photosensitive material.

A particularly versatile observing possibility, especially as regards the further processing of the data received, is obtained when the light deviated for the visual observation is supplied to a photoelectric transducer which generates corresponding electric signals so that the image of the point-shaped sample area can be displayed by electronic means, for instance on a television monitor. A photoelectric transducer particularly suited for this purpose is found in a charge-coupled element (CCD) of the type used in modern television cameras. One obtains in this manner an electric signal which is particularly well suited for digital storage and processing.

In addition, the use of opto-electronic processing for the visual observation of the sample under investigation offers the advantage that photoelectric transducers operating in the infrared range of the type known, for instance, in connection with noctovisers can be used. In this case, the visual observation of the point-shaped area of the sample may be effected using the infrared light which is anyway available so that there is no need for the additional light source 18 which emits light in the visible range.

In the examples described above, the optical elements employed, i.e. mirrors, lenses, etc., are shown in fixed arrangement, but it goes without saying that other arrangements may be used, in particular if different image scales are to be achieved, where several such optical elements of different designs can be mounted on turret means or slides so that the optical element desired at any time can be brought into the operating position by turning the turret means or displacing the slide.

We claim:

1. An infrared spectrometer comprising:
   a source for generating a first beam of infrared radiation;
   first optical means for focusing said first beam in an approximately point-shaped area upon the surface of a sample under investigation;
   an infrared light-sensitive detector;
   second optical means for focusing upon said detector at least a portion of a second beam of infrared radiation reflected from said area upon indication of said first beam;
   visual observation means for visually viewing said area; and
   third optical means arranged for reflecting at least a portion of said second beam onto said visual observation means.

2. An infrared spectrometer in accordance with claim 1, characterized in that an intermediate focus is projected upon the sample (20, 64).

3. An infrared spectrometer in accordance with claim 2, characterized in that an adjustable diaphragm aperture (13) is provided at the location of the intermediate focus.

4. An infrared spectrometer in accordance with claim 2, characterized in that the first optical means comprise a collimator mirror (11) for focussing the light arriving in a parallel beam from a light source (10) upon the intermediate focus.

5. An infrared spectrometer in accordance with claim 2, characterized in that at least the first optical means comprise in addition a mirror system, in particular a mirror lens (16, 17; 60, 61), for focussing the diverging beam of light (15) emerging from the diaphragm aperture (13) upon the sample (20).

6. An infrared spectrometer in accordance with claim 2, characterized in that at least the first optical means comprise in addition a lens system for focussing the diverging beam of light (15) emerging from the diaphragm aperture (13) upon the sample (20).

7. An infrared spectrometer in accordance with claim 1, characterized in that the axis of the beam of light inciding upon the sample (20) extends substantially vertically relative to the sample surface.

8. An infrared spectrometer in accordance with claim 1, characterized in that the axis of beam of light inciding upon the sample (20) extends substantially at an oblique angle relative to the sample surface.

9. An infrared spectrometer in accordance with claim 5, characterized in that some of the first optical means serve simultaneously as second optical means, in particular that the light reflected by the sample surface is picked up by the same mirror lens (16, 17) or lens system which serves also for focussing the beam of light (15) emerging from the diaphragm aperture (13) upon the sample (20).

10. An infrared spectrometer in accordance with claim 5, characterized in that the second optical means comprise a deviating mirror (23) which is arranged behind the diaphragm aperture (13) and preferably mounted to pivot about an axis (22) located outside the diverging beam of light (15), for deviating the light reflected by the mirror lens (16, 17) or lens system in the direction of the diaphragm aperture (13).

11. An infrared spectrometer in accordance with claim 5, characterized in that the second optical means comprise a beam splitter (96) which is arranged behind the diaphragm aperture (13) and preferably mounted to pivot about an axis (95) located outside the diverging beam of light (15), for deviating the light reflected by the mirror lens (16, 17) or lens system in the direction of the diaphragm aperture (13).

12. An infrared spectrometer in accordance with claim 5, characterized in that the mirror system of the first optical means comprises a first mirror lens (92, 93) for parallelizing the diverging beam of light (91) emerging from the diaphragm aperture (13) and a second mirror lens (92a, 93a) for focussing the parallelized beam of light (94) and that the second optical means comprise a deviating mirror (23) which is arranged within the parallelized beam of light (94) and preferably mounted to pivot about an axis (22) located outside the parallelized beam of light (94), for deviating the light reflected by the second mirror lens (92a, 93a) in the direction of the diaphragm aperture (13).

13. An infrared spectrometer in accordance with claim 10, characterized in that the beam of light (24) deviated by the deviating mirror (23) is focussed upon a detector (26) by a collimator mirror (25).

14. An infrared spectrometer in accordance with claim 5, characterized in that an annular mirror (35) is arranged within the beam of light (15) reflected by the mirror lens (16, 17) or lens system in the direction of the diaphragm aperture (13), in a plane inclined relative to the axis of the beam of light 15, the reflecting annular face of the annular mirror (35) being arranged in a marginal area of the beam of light (15) and facing the mirror lens (16, 17) or lens system.

15. An infrared spectrometer in accordance with claim 5, characterized in that a deviating mirror (50) is arranged in a plane inclined relative to the axis of the beam of light (32) in the dark space (49) of the toroidal beam of light (32) which is focussed upon the sample (20) by the mirror lens (16, 17).

16. An infrared spectrometer in accordance with claim 5, characterized in that a second mirror lens (67, 68) or lens system whose axis is inclined relative to the axis of the first mirror lens (60, 61) or lens system is provided above the sample (64) for picking up the light reflected by the sample (64), and that preferably third optical means for visually observing the sample are provided along an axis extending vertically to the sample surface.

17. An infrared spectrometer in accordance with claim 1, characterized in that the point-shaped area (19) is formed in said visual observation means.

18. An infrared spectrometer in accordance with claim 17, characterized in that the third optical means comprise a preferably pivotally mounted deviating mirror (28, 30, 31, 72) arranged in the beam path of the light reflected by the sample (20, 64).

19. An infrared spectrometer in accordance with claim 1, characterized in that the second optical means pick up the light directly reflected by the sample (20, 64).

20. An infrared spectrometer in accordance with claim 1, characterized in that the second optical means pick up the diffuse light reflected by the sample (20, 64).

21. An infrared spectrometer in accordance with claim 1, characterized in that fourth optical means (81 to 85) are additionally provided below the sample (80), for picking up the light transmitted by the sample (80), preferably simultaneously with the picking-up of the reflected light.

22. An infrared spectrometer in accordance with claim 1, characterized in that the area (99) of the sample (20) has finite dimensions and is projected upon a line or surface detector (97) comprising a matrix (98) of detector elements which can be scanned in an integrating or selective manner by an evaluator (32, 33).

23. An infrared spectrometer in accordance with claim 22, characterized in that the measuring values picked up by the matrix (98) can be displayed on a monitor either totally or selectively, or even discretely in groups.

24. An infrared spectrometer in accordance with claim 1, characterized in that the light received from the sample (20, 64) is evaluated according to a Fourier transformation (FT) method.

25. The infrared spectrometer in accordance with claim 1, characterized in that the path of said reflected second beam is in part coincident with the path of said first beam.

26. The infrared spectrometer in accordance with claim 25, characterized in that said second optical means includes mirror means located in the coincident path of said first and second beams and arranged to deviate a portion of said second beam from said coincident path.

27. The infrared spectrometer in accordance with claim 1, characterized in that said third optical means is located in the path of said second beam.

28. The infrared spectrometer in accordance with claim 26, characterized in that said third optical means is located in the coincident path of said first and second beams.

29. The infrared spectrometer in accordance with claim 28, characterized in that the mirror means of said second optical means is located between the sample and said third optical means along the axis of said coincident path.

30. An infrared spectrometer comprising:
a source for generating a first beam of infrared radiation;
first optical means for focusing said first beam in an approximately point-shaped area upon the surface of a sample under investigation;
an infrared light-sensitive detector;
second optical means including at least part of said first optical means for focusing upon said detector a portion of a second beam of infrared radiation reflected from said area upon incidation of said first beam, such that the path of said second beam is in part coincident with the path of said first beam;
visual observation means for visually viewing said area; and
third optical means located in the path of said second beam and arranged for reflecting at least a portion of said second beam onto said visual observation means.

31. The infrared spectrometer in accordance with claim 30, characterized in that said third optical means is located in the coincident path of said first and second beams.

* * * * *